US009556333B2

(12) United States Patent
Clay

(10) Patent No.: US 9,556,333 B2
(45) Date of Patent: Jan. 31, 2017

(54) BIODEGRADABLE POLYMER FORMULATIONS

(71) Applicant: Warsaw Orthopedic, Inc., Warsaw, IN (US)

(72) Inventor: Danielle L. Clay, Pleasant Prairie, WI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/664,531

(22) Filed: Mar. 20, 2015

(65) Prior Publication Data

US 2015/0209433 A1 Jul. 30, 2015

Related U.S. Application Data

(63) Continuation-in-part of application No. 14/286,673, filed on May 23, 2014, now Pat. No. 9,242,004, which is a continuation of application No. 13/462,395, filed on May 2, 2012, now Pat. No. 8,735,504.

(51) Int. Cl.
| | |
|---|---|
| *C08L 67/04* | (2006.01) |
| *C08J 3/00* | (2006.01) |
| *C08G 85/00* | (2006.01) |
| *A61K 47/34* | (2006.01) |
| *B29C 45/00* | (2006.01) |
| *A61K 31/4168* | (2006.01) |

(52) U.S. Cl.
CPC ............... *C08L 67/04* (2013.01); *A61K 47/34* (2013.01); *C08G 85/002* (2013.01); *C08J 3/00* (2013.01); *A61K 31/4168* (2013.01); *B29C 45/00* (2013.01); *B29K 2995/006* (2013.01); *C08J 2367/04* (2013.01)

(58) Field of Classification Search
CPC .. A61K 31/4168; A61K 47/34; C08G 85/002; C08L 67/04; C08J 3/00; C08J 2367/04; B29C 45/00; B29K 2995/006
See application file for complete search history.

(56) References Cited

U.S. PATENT DOCUMENTS

| | | | |
|---|---|---|---|
| 4,810,775 A * | 3/1989 | Bendix | A61L 27/18 210/768 |
| 5,759,583 A | 6/1998 | Iwamoto et al. | |
| 5,942,241 A | 8/1999 | Chasin et al. | |
| 6,069,129 A | 5/2000 | Sandberg et al. | |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,326,025 B1 | 12/2001 | Sigler et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,773,714 B2 | 8/2004 | Dunn et al. | |
| 6,921,541 B2 | 7/2005 | Chasin et al. | |
| 7,287,983 B2 | 10/2007 | Ilan | |
| 7,727,954 B2 | 6/2010 | McKay | |
| 7,947,803 B2 | 5/2011 | Hong et al. | |
| 8,735,504 B2 | 5/2014 | Clay | |
| 2002/0009454 A1 | 1/2002 | Boone et al. | |
| 2002/0090398 A1 | 7/2002 | Dunn et al. | |
| 2004/0022859 A1 * | 2/2004 | Chen | A61K 9/0024 424/486 |
| 2004/0072799 A1 | 4/2004 | Li et al. | |
| 2004/0082540 A1 | 4/2004 | Hermida Ochoa | |
| 2004/0109893 A1 | 6/2004 | Chen et al. | |
| 2004/0214793 A1 | 10/2004 | Hermida Ochoa | |
| 2004/0219214 A1 | 11/2004 | Gravett et al. | |
| 2005/0142163 A1 | 6/2005 | Hunter et al. | |
| 2005/0175709 A1 | 8/2005 | Baty, III et al. | |
| 2005/0186261 A1 | 8/2005 | Avelar et al. | |
| 2005/0197293 A1 | 9/2005 | Mellis et al. | |
| 2005/0288620 A1 | 12/2005 | Shippert | |
| 2006/0074422 A1 | 4/2006 | Story et al. | |
| 2006/0104966 A1 | 5/2006 | Green et al. | |
| 2006/0105026 A1 | 5/2006 | Fortune et al. | |
| 2006/0148903 A1 | 7/2006 | Burch et al. | |
| 2006/0153815 A1 | 7/2006 | Seyda et al. | |
| 2006/0189944 A1 | 8/2006 | Campbell et al. | |
| 2006/0228391 A1 | 10/2006 | Seyedin et al. | |
| 2006/0253094 A1 | 11/2006 | Hadba et al. | |
| 2007/0021358 A1 | 1/2007 | Edelman et al. | |
| 2007/0066864 A1 | 3/2007 | Forde | |
| 2007/0104769 A1 | 5/2007 | Feng et al. | |
| 2007/0156180 A1 | 7/2007 | Jaax et al. | |
| 2007/0202074 A1 | 8/2007 | Shalaby | |
| 2007/0224235 A1 | 9/2007 | Tenney et al. | |
| 2007/0243225 A1 | 10/2007 | McKay | |
| 2007/0243228 A1 | 10/2007 | McKay | |
| 2007/0253994 A1 | 11/2007 | Hildebrand | |
| 2007/0286891 A1 | 12/2007 | Kettlewell et al. | |
| 2007/0299155 A1 | 12/2007 | Carpenter et al. | |
| 2008/0009830 A1 | 1/2008 | Fujimoto et al. | |

(Continued)

OTHER PUBLICATIONS

Onesti, G., et al.; Circulation Research, 1971, vol. 28, p. II-53 to II-69.*

*Primary Examiner* — Robert Jones, Jr.
(74) *Attorney, Agent, or Firm* — Sorell Lenna & Schmidt LLP

(57) ABSTRACT

A polymeric material which can degrade in less than 6 months is provided. The polymeric material includes a plurality of biodegradable polymers having a polydispersity or molecular weight distribution from about 1.5 to about 2.5. A method of making the polymeric material is also provided. The method includes mixing a plurality of biodegradable polymers together to form a polymeric mixture, wherein the polymeric mixture has a polydispersity from about 1.5 to about 2.5. The application of this polymeric material to medical devices such as and implantable depots is described. A method for treating acute pain in an organism to reduce, prevent or treat pain utilizing these polymeric materials having a polydispersity or molecular weight distribution from about 1.5 to about 2.5 is also provided.

17 Claims, No Drawings

(56) References Cited

U.S. PATENT DOCUMENTS

| | | |
|---|---|---|
| 2008/0038351 A1 | 2/2008 | Beals et al. |
| 2008/0039547 A1 | 2/2008 | Khatri et al. |
| 2008/0039548 A1 | 2/2008 | Zavatsky et al. |
| 2008/0091207 A1 | 4/2008 | Truckai et al. |
| 2008/0096975 A1 | 4/2008 | Guan et al. |
| 2009/0018575 A1 | 1/2009 | Fortune et al. |
| 2009/0030451 A1 | 1/2009 | Hadba et al. |
| 2009/0044895 A1 | 2/2009 | Fortune et al. |
| 2009/0287129 A1 | 11/2009 | Boehringer et al. |
| 2010/0003329 A1 | 1/2010 | Elisseeff |
| 2010/0080838 A1 | 4/2010 | Stopek |
| 2010/0137550 A1 | 6/2010 | Enderle et al. |
| 2010/0173843 A1 | 7/2010 | Hnojewyj |
| 2010/0215659 A1 | 8/2010 | Ladet |
| 2011/0105641 A1 | 5/2011 | Khatri et al. |
| 2011/0111034 A1 | 5/2011 | Wang et al. |

\* cited by examiner

BIODEGRADABLE POLYMER FORMULATIONS

This application claims the benefit of the filing date of and is a continuation-in-part of U.S. application Ser. No. 14/286,673, filed May 23, 2014, entitled "Methods for Preparing Polymers Having Low Residual Monomer Content", which is a continuation of U.S. application Ser. No. 13/462,395, filed on May 2, 2012, now U.S. Pat. No. 8,735,504. These entire disclosures are hereby incorporated by reference into the present disclosure.

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Localized delivery of therapeutic agents has become increasingly more popular over the years because it has several advantages over more conventional routes of drug delivery such as oral delivery. Localized delivery has the advantage of allowing the therapeutic agent to be implanted directly at the site where drug action is needed. This becomes especially important for drugs that have unwanted systemic side effects.

Localized delivery of therapeutic agents has the advantage of protecting the therapeutic agent from breakdown due to harsh physiological environments (e.g., gastric and liver enzymes) and thus improves the drug's stability in vivo. This particular feature makes this technology particularly attractive for the delivery of labile drugs such as proteins and peptides. Localized delivery also improves patient compliance. For example, therapeutic agents can be encapsulated and delivered locally allowing the drug to be released over extended periods (e.g., 6 months or longer) and hence eliminates the need for multiple injections. This feature can improve patient compliance especially for drugs for chronic indications, requiring frequent injections.

In the past, localized repeat delivery of therapeutic agents has been used to treat chronic debilitating diseases such as osteoarthritis. Osteoarthritis is a chronic condition that affects millions of people in the world, and it is a type of arthritis that is caused by the chronic breakdown and eventual loss of cartilage in one or more joints. Osteoarthritis often affects synovial joints, such as the knees, hips, fingers, thumbs, neck, and spine. Severe forms of the disease are extremely disabling and restrict a patient's lifestyle. Localized delivery via intraarticular injection of corticosteroids, hyaluronan or hylan provides some short term relief in controlling the pain symptoms of osteoarthritis.

Sciatica, another debilitating disease, can be a painful condition associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. In the past, localized delivery of corticosteroids (e.g., epidural) has been used to provide short term relief of the inflammation and pain associated with sciatica.

Newer methods are currently being investigated for treatment of chronic debilitating diseases utilizing localized delivery of drug depots for release at various release rates. In these treatments typically the drug depot is delivered locally to the treatment site and the drug is released from the depot in a relatively uniform dose over weeks, months or even years. Localized delivery of drug depots is becoming especially important and popular in modulating the immune, inflammation and/or pain responses in treatment of chronic diseases.

The slow degradation of polymers often limits their performance in medical device applications. Making biomedical devices involves the use of a broad variety of polymers. Many devices need biodegradable polymers. For example, polylactides can be used for degradable orthopedic rods, screws and plates as well drug delivery products, for example, implantable depots. Biodegradable polymers for tissue engineered drugs containing implantable depots may need to degrade and disappear after the drugs are released.

Sometimes after the drug depot is implanted at the treatment site, unfortunately, the drug depot may migrate from the implant site as physiological conditions change (e.g., repair and regeneration of cells, tissue in growth, and movement at implant site, etc.). At times, this may reduce efficacy of the drug as the drug depot migrates away from the implant site and lodges in a distant site. If this occurs, often the drug depot will have to be removed from the distant site and be reinserted causing additional physical and psychological trauma to a patient. In some cases, if the drug depot migrates into a joint, the drug depot may inhibit movement. In more severe cases, if the drug depot migrates in a blood vessel, it may restrict blood flow causing an ischemic event (e.g., embolism, necrosis, infarction, etc.), which could be detrimental to the patient.

Therefore, new drug depot compositions and methods are needed, which can allow not only for accurate and precise placement of a drug depot with minimal physical and psychological trauma to a patient, but also provide various rates of degradation to release drug at the desired rate and degrade in time.

SUMMARY

Polymeric materials are provided comprising a plurality of biodegradable polymers having a polydispersity index or molecular weight distribution from about 1.5 to about 2.5. In some embodiments, the polymeric materials have a polydispersity index of greater than 2.

In some embodiments, it is contemplated that the polymeric materials comprise, consist essentially of, or consist of a polymeric mixture or blend of a first polymer in an amount of about 10%, a second polymer in an amount of about 20%, a third polymer in an amount of about 50% and a fourth polymer in an amount of about 20%. In other embodiments, the plurality of biodegradable polymers comprises a first polymer in an amount from about 5% to about 15%, a second polymer in an amount of about 15% to about 25%, a third polymer in an amount of about 45% to about 55% and a fourth polymer of about 15% to about 25% by weight.

In some embodiments, the polymeric materials comprise, consist essentially of, or consist of a polymeric mixture or blend of a first poly(D,L-lactide) having an inherent viscosity from about 0.15 to about 0.25 dL/g and ester end groups in an amount of about 10%, a second poly(D,L-lactide) having an inherent viscosity from about 0.40 to about 0.50 dL/g and carboxylic acid end groups in an amount of about 20%, a third poly(D,L-lactide) having an inherent viscosity from about 0.40 to about 0.50 dL/g and ester end groups in an amount of about 50% and a fourth poly(D,L-lactide) having an inherent viscosity from about 0.60 to about 0.80 dL/g and ester end groups in an amount of about 20%.

Compositions and methods are provided comprising clonidine or its pharmaceutically acceptable salts that are administered in order to treat pain and/or inflammation. The compositions and methods may, for example, be used to treat pain due to a spinal disc herniation (i.e., sciatica), spondilothesis, stenosis, osteoarthritis, carpal/tarsal tunnel syndrome, tendonitis, temporomandibular joint disorder (TMJ), discogenic back pain, joint pain or inflammation.

In some embodiments, there is an implantable medical device for reducing or treating pain in a patient in need of such treatment, the implantable medical device comprising clonidine in an amount from about 1.0 wt. % to about 20 wt. % of the implantable medical device, and a plurality of biodegradable polymers having a polydispersity index greater than 2, wherein the implantable medical device can degrade and disappear in less than 6 months.

In other embodiments, there is an implantable drug depot for treating chronic pain in a patient in need of such treatment, the implantable medical device comprising clonidine hydrochloride in an amount from about 0.01 wt. % to about 20 wt. % of the implantable drug depot, and a plurality of biodegradable polymers comprising poly(D-lactide), poly(D,L-lactide), poly(L-lactide) wherein the implantable drug depot releases the clonidine over a period of at least 30 days to less than 6 months and the plurality of biodegradable polymers degrade and disappear in less than 6 months.

In some embodiments, there is a method for treating chronic pain in a patient in need of such treatment, the method comprising administering to a target tissue site beneath the skin of the patient an implantable drug depot comprising a plurality of biodegradable polymers having a polydispersity index of greater than 2, the implantable drug depot degrading an disappearing in less than 6 months.

In some embodiments, the drug depot may: (i) consist of only the clonidine (or one or more of its pharmaceutically acceptable salts) and the plurality of biodegradable polymers having a polydispersity greater than 2; or (ii) consist essentially of the clonidine (and/or one or more of its pharmaceutically acceptable salts) and the plurality of biodegradable polymers having a polydispersity greater than 2; or (iii) comprise the clonidine (and/or one or more of its pharmaceutically acceptable salts), and the biodegradable polymer(s) and one or more other active ingredients, surfactants, excipients or other ingredients or combinations thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

An implantable medical device includes that the device can be implanted into the human body. In various embodiments, the medical device is not implanted into the eye. The medical device allows release of the drug or therapeutic agent. A medical device includes a drug depot, which can be solid, semi-solid or in gel form.

The term "implantable" as utilized herein refers to a biocompatible depot (e.g., device) retaining potential for successful placement within a mammal. The expression "implantable depot" and expressions of the like import as utilized herein refers to an object implantable through surgery, injection, or other suitable means whose primary function is achieved either through its physical presence or mechanical properties.

A "drug depot" is the composition in which a drug or active pharmaceutical ingredient is administered to the body. Thus, a drug depot may comprise a physical structure (e.g., strip, pellet) to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot (e.g., fiber) provides an optimal drug concentration gradient of the therapeutic agent at a distance of up to about 0.01 cm to about 20 cm from the administration site and comprises clonidine. A drug depot may also include a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired, in some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In some embodiments, the drug depot has a modulus of elasticity in the range of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$.

The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. Generally, the term "biodegradable polymer" means a synthetic or a naturally derived biodegradable, biocompatible polymer that may be absorbed (resorbed) once implanted in a living mammalian body. In the present application biodegradable polymer refers to synthetically derived polymers. Synthetic biodegradable polymers include, but are not limited to, polyethylene glycol (PEG), polyvinyl alcohol (PVA), polyorthoester (POE), polylactic acid (PLA), polyglycolic acid (PGA), polyactic-glycolic acid (PLGA), D-lactide, D,L-lactide co-caprolactone, L-lactide-co-caprolactone, D,L-lactide-co-glycolide-co-caprolactone, poly(D,L-lactide-co-caprolactone), poly(L-lactide-co-caprolactone), poly(D-lactide-co-caprolactone), poly(D,L-lactide), poly(D,L-lactide), poly(L-lactide), poly(esteramide) or a combination thereof. Suitable polymers that can be used in the present application are described in U.S. application Ser. No. 13/462,395, filed on May 2, 2012, now U.S. Pat. No. 8,735,504. The entire disclosure is hereby incorporated by reference into the present disclosure.

By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in viva of the drug depot, or a fiber or component thereof, or as the result of metabolic transformation or dissolution of the therapeutic agent(s) or conjugates of therapeutic agent(s).

The two types of formulations (sustain release and immediate release) may be used in conjunction. The sustained release and immediate release may be in one or more of the same fiber. In various embodiments, the sustained release and immediate release may be part of separate drug depots. For example a bolus or immediate release formulation of clonidine may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four to seventy-two hours after implantation. "Initial burst" or "burst effect" "burst release" or "bolus dose" refers to the release of therapeutic agent from the depot (e.g., fiber, pellet, strip, etc.) during the first twenty-four hours to seventy-two hours after the depot (e.g., fiber) comes in contact with an aqueous fluid (e.g., interstitial fluid, synovial fluid, cerebral spinal fluid, etc.). The "burst effect" is believed to be due to the increased release of therapeutic agent from the drug depot. In some embodiments, the drug depot has one or more burst release surfaces that releases about 10%, 15%, 20%, 25%, 30%, 35%, 45%, to about 50% of the drug over 24 or 48 hours.

In alternative embodiments, the drug depot is designed to avoid or reduce this initial burst effect (e.g., by applying an outer polymer coating to the drug depot).

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosage of clonidine may be used to prevent, treat or relieve the symptoms of pain and/or inflammation for different diseases or conditions. These disease/conditions may comprise post-operative pain, oral-facial diseases, bursitis, tendonitis, chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis. In some embodiments, the drug depot containing the therapeutic agent is not administered in, to or near the eye.

One chronic condition is sciatica. In general, sciatica is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the clonidine may be used to reduce, treat, or prevent sciatic pain and/or inflammation by locally administering the clonidine at one or more target tissue sites (e.g., nerve root, dorsal root ganglion, focal sites of pain, at or near the spinal column, etc.).

In some embodiments, the drug depot can be used to treat one or more target tissue sites that are involved in conditions/diseases, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, a surgical wound site or an incision site, postoperative pain or the like.

The term "implantable" as utilized herein refers to a biocompatible device (e.g., pellet or drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy or constipation may be reduced or eliminated. In some embodiments, the depot is not to be administered at or near the eye.

The term "mammal" refers to organisms from the taxonomy class "mammalian," including but not limited to humans, other primates such as chimpanzees, apes, orangutans and monkeys, rats, mice, cats, dogs, cows, or horses.

The term "polydispersity index" or "polydispersity" refers to the ratio of the weight average molecular weight ($M_w$) of the polymer to the number-average molecular weight ($M_n$) of the polymer or ($M_w/M_n$).

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, for example, mcg/hr, mcg/day, 10% per day for ten days, etc. As persons of ordinary skill know, a release rate profile may, but need not, be linear. By way of a non-limiting example, the drug depot may be a ribbon-like fiber that releases the drug over a period of time.

The term "solid" is intended to mean a rigid material, while, "semi-solid" is intended to mean a material that has some degree of flexibility, thereby allowing the depot (e.g., fiber, strip, pellet, etc.) to bend and conform to the surrounding tissue requirements.

"Targeted delivery system" provides delivery of one or more drugs depots (e.g., fibers, strip, pellet, etc.) at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to polyethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "PEA" refers to poly(ester)amides.

The abbreviation "POE" refers to poly(orthoester). The above polymers or combination of polymers can be in the drug depot (e.g., fiber, strip, pellet, etc.).

Polymeric Material Having Reduced Degradation Time

Polymeric devices are made from polymeric materials which need to degrade over days or years. In the synthesis of biodegradable polymers such as homopolymers or copolymers based on lactide (L-lactide, D-lactide, DL-lactide, meso-lactide), glycolide, epsilon-caprolactone, dioxanone, trimethylene carbonate, delta-valerolactone, gamma-butyrolactone the presence of monomers helps in accelerating the degradation of biodegradable polymers in the body. In many instances monomers decompose more rapidly than biodegradable polymers on exposure to moisture. Consequently, the implantation of monomer-containing biodegradable polymers in medical devices would therefore lead to a more accelerated breakdown of the material in the body.

Polymers may have broad molecular weight distributions. For example, the biodegradable polymers of this application can provide a polymer composition or blend similar to 100% poly(D,L-lactide) or 100DL 5E that has an inherent viscosity of 0.45-0.55 dL/g, has a molecular weight from about 60 kDa and it contains ester end groups. The composition of 100DL 5E has a negligible amount of monomeric content which accounts for prolonged polymer degradation time of about 12 months, a desirable property for some medical devices. It has been surprisingly discovered that by combining biodegradable polymers of a certain molecular distribution and having increased monomer content, polymeric materials or blends can be obtained which have a polydispersity index greater than 2 and can degrade in less than 6 months, a property desirable for implantable drug depots useful in treating chronic diseases such as sciatica and osteoarthritis.

The breadth of the molecular weight distribution of a polymer can be measured by the polydispersity index ($M_w/M_n$) of the polymer. The polydispersity index or polydispersity is the ratio of the weight-average molecular weight (Mw) of the polymer to the number-average molecular weight ($M_n$) of the polymer. The weight-average molecular weight and the number-average molecular weight of a polymer can be determined by analytical methods, such as gel permeation chromatography. Similarly, the number-average molecular weight ($M_n$) may be correlated to the intrinsic viscosity:

[η]=(1.019×10−3)·(Mn 0.659), wherein the parameters were also determined using gel permeation chromatography. Once the weight-average and number-average molecular weights have been determined, the polydispersity index is easily calculated by dividing the weight-average molecular weight by the number average molecular weight, $M_w/M_n$. More conveniently, however, the molecular weight is determined using a standardized intrinsic viscosity assay (ISO 1628-1). The value for the intrinsic viscosity ([η]) thus obtained (expressed in dL/g) may be converted into the weight average molecular weight ($M_w$) by using the well-known Mark-Houwink expression.

[η]=K($M_w$)$^α$, wherein K and α are specific parameters.

Similarly, the number-average molecular weight ($M_n$) may be correlated to the intrinsic viscosity:

[η]=(1.019×10−3)($M_n$ 0.659), wherein the parameters were also determined using gel permeation chromatography. A hypothetically monodisperse polymer has a polydispersity index of 1.000. Polymers with broad molecular weight distributions have higher polydispersity indices and while polymers with narrow molecular weight distributions have lower polydispersity indices.

In some embodiments, by increasing the monomer content of the poly(lactide) polymers, polymer blends are provided having a polydispersity index greater than 1.5 or 1.6 or 1.7 or 1.8 or 1.9 or 2.0, 2.1 or 2.2 or 2.3 or 2.4 or 2.5. This allows the desired drug release from the medical device (e.g., drug depot) for treatment of chronic conditions, such as for example, sciatica, osteoarthritis, etc.

As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion). Polymer hydrolysis prompted by reaction with water in tissues is one mechanism which results into degradation of biodegradable polymers. In some embodiments, some poly(D,L-lactide) polymers have ester end groups (e.g., methyl or ethyl ester end groups), which are hydrophobic and as a result do not facilitate polymeric degradation by hydrolysis. Other poly(D,L-lactide) polymers have carboxylic acid end groups which are hydrophilic which facilitate polymeric degradation by hydrolysis.

Monomer content can be controlled in several ways including the selection of commercial biodegradable polymers with a desirable level of monomer concentration. Biodegradable polymers that are useful in this application include 100DL 2E, 100DL, 4A, 100DL 4E, 100DL 4.5A, 100DL 4.5E, 100DL 5A, 100DL 5E, 100DL 7E or mixtures thereof, all available from Evonik Industries, Birmingham, Ala., under the trademark RESOMER® 100DL 2E is a polymer that has an inherent viscosity of 0.15-0.25 dL/g and a molecular weight of about 7 kDa. It contains 100% poly(D,L-lactide) and has ester end groups. 100DL 4A is a polymer that has an inherent viscosity of 0.35-0.45 dL/g and a molecular weight of about 40 kDa. It contains 100% poly(D,L-lactide) and has carboxylic acid end groups. 100DL 4E is a polymer that has an inherent viscosity of 0.35-0.45 dL/g and a molecular weight of about 40 kDa. It contains 100% poly(D,L-lactide) and has ester end groups. 100DL 4.5A is polymer that has an inherent viscosity of 0.40-0.50 dL/g and a molecular weight of about 50 kDa. It contains 100% poly(D,L-lactide) and has carboxylic acid end groups. 100DL 4.5E is polymer that has an inherent viscosity of 0.40-0.50 dL/g and a molecular weight of about 50 kDa. It contains 100% poly(D,L-lactide) and has ester end groups. 100DL 5A is polymer that has an inherent viscosity of 0.45-0.55 dL/g and a molecular weight of about 60 kDa. It contains 100% poly(D,L-lactide) and has carboxylic acid end groups. 100DL 5E is polymer that has an inherent viscosity of 0.45-0.55 dL/g and a molecular weight of about 60 kDa. It contains 100% poly(D,L-lactide) and has ester end groups. 100DL 7E is polymer that has an inherent viscosity of 0.60-0.80 dL/g and has a molecular weight from about 80 kDa to about 90 kDa. It contains 100% poly(D,L-lactide) and has ester end groups.

In some embodiments, monomer content can be increased through addition of monomer to a scaffolding polymer in the extrusion step utilized in the preparation of the polymeric material. For example, for the polymers of the molecular weight distribution described above, monomer content can vary from about 0.01% to about 2.0%. In various embodiments, the monomer content can be 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.0%9, 0.095%, 0.1%, 0.15%, 0.2%, 0.25%, 0.3%, 0.35%, 0.4%, 0.4%5, 0.5%, 0.55%, 0.6%, 0.65%, 0.7%, 0.75%, 0.8%, 0.85%, 0.9%, 0.95%, 1.0%, 1.1%, 1.15%, 1,2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, or 2.0% by weight of the average molecular weight of the poly(D,L-lactide) polymer.

In various embodiments, the polymeric material of this application comprises biodegradable polymers having an average molecular weight from about 7 kDA to about 80 kDa. In other embodiments, the polymeric material comprises biodegradable polymers which have a molecular weight of about 60 kDa.

In some aspects, the polymeric material of this application comprises a plurality of biodegradable polymers forming a polymeric blend having a first polymer in an amount of about 10%, a second polymer in an amount of about 20%, a third polymer in an amount of about 50% and a fourth polymer of about 20% by weight. In other aspects, the polymeric blend of this application comprises a plurality of biodegradable polymers having a first polymer in an amount from about 5% to about 15%, a second polymer in an amount of about 15% to about 25%, a third polymer in an amount of about 45% to about 55% and a fourth polymer of about 15% to about 25% by weight.

In some embodiments, the plurality of biodegradable polymers usefill for the polymeric blends comprises 100DL 2E in an amount of about 10%, 100DL 4.5A in an amount of about 20%, 100DL 4.5E in an amount of about 50% and 100DL 7E in an amount of about 20% by weight. In other aspects, the polymeric blend of this application comprises a plurality of biodegradable polymers having a first polymer in an amount from about 5% to about 15%, a second polymer in an amount of about 15% to about 25%, a third polymer in an amount of about 45% to about 55% and a fourth polymer of about 15% to about 25% by weight. These polymer blends can be used to increase or decrease monomer content of the total blend of polymers to obtain the desired drug release profile so that the medical device (e.g., drug depot) will degrade during release and be eliminated by the body over time.

In various aspects, the plurality of biodegradable polymers forming the polymeric materials or blends of this application comprises one or more monomers, co-monomers or polymers comprising poly(lactide-co-glycolide) (PLGA), polylactide (PLA), polyglycotide (PGA), D-lactide, D,L-lactide, L-lactide, D,L-lactide co-caprolactone, D,L-lactide-co-ϵ-caprolactone, L-lactide-co-caprolactone, L-lactide-co-ϵ-caprolactone, D,L-lactide-co-glycolide-co-caprolactone, D,L-lactide-co-glycolide-co-ϵ-caprolactone, poly(D,L-lactide-co-caprolactone), poly(L-lactide-co-caprolactone), poly(D,L-lactide-co-caprolactone), lactide-co-ϵ-caprolactone), poly(L-lactide-co-ϵ-caprolactone), poly(D-lactide-co-ϵ-caprolactone) poly(D,L-lactide), poly(D-lactide), poly(L-lactide), poly(esteramide) or a combination thereof.

In some embodiments, the polymeric materials or blends of this application can be used to prepare medical devices that require a degradation time of less than 6 months. The polymeric material useful for such medical devices comprises a plurality of polymers having a polydispersity: or molecular weight distribution greater than 1.5 or 1.6 or 1.7 or 1.8 or 1.9 or 2.0 or 2.2 or 2.3 or 2.4 or 2.5. In some embodiments, the medical device can be an implantable depot as described below. The implantable depot can be utilized to release a drug or drugs for treatment of.

Methods for the preparation of polymeric materials or blends having a degradation time of less than 6 months and a polydispersity greater than 2 are also provided. In some embodiments, a plurality of biodegradable polymers comprising a first polymer in an amount of about 10%, a second polymer in an amount of about 20%, a third polymer in an amount of about 50% and a fourth polymer of about 20% by weight is mixed as a powder blend using mixing techniques such as, for example, granulation, levitation, milling, or the like. In other embodiments, the plurality of biodegradable polymers described in this application are mixed and then dissolved in an organic or inorganic solvent, as applicable. Useful solvents comprise without limitation n-hexane, cyclohexane, heptanes, methylene chloride, ethyl acetate, acetone or combinations thereof. In other embodiments the solvents also include polyethylene glycols as esters or ethers, polyethoxylated fatty acids, hydroxylated fatty acids, fatty alcohols, polyethoxylated castor oil, polyethoxylated hydrogenated castor oil, polyethoxylated fatty acid from castor oil, polyethoxylated fatty acid from hydrogenated castor oil, Cremophor, Myrj, Polyoxyl 40 stearate, Emerest 2675, Lipal 395, Tween, Span and HCO 50, glycerin, N,N-dimethylacetamide, ethyl alcohol, denatured alcohol, ester, acetone, transcutol or a combination thereof.

In some embodiments an anti-solvent can be added to the polymeric mixture or blend to separate the mixture of biodegradable polymers or polymeric blend having a polydispersity greater than 2 from other polymers, co-monomers or monomers. Useful anti-solvents comprise without limitation water, ethanol, methanol, supercritical carbon dioxide, supercritical nitrogen, supercritical water or mixtures thereof.

Clonidine Compounds

When referring to clonidine, unless otherwise specified or apparent from context it is understood that the inventors are also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, mane, benzoic, glycollic, gluconic, gulonic, succinic, arylsulfonic, e.g., p-toluenesulfonic acids, or the like.

Further, when referring to clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non-limiting example, when formulating clonidine with poly(orthoesters) it may be desirable to use the clonidine base formulation. By contrast, when formulating clonidine with PLGA, it may be desirable to use the HCl salt form. In some embodiments, the clonidine may be incorporated into a polymer core with a polymer and then coated with the same or different polymer.

Pharmaceutically acceptable salts of clonidine include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, dimethylaminoethanol, ethanolamine, ethylenediamine, N-ethyl-morpholine, N-ethylpiperidine glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, rube, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, stearic, arachidic or the like.

In some embodiments, in order to reduce the solubility of the clonidine to assist in obtaining a controlled release depot (e.g., fiber, strip, pellet, etc.) effect, clonidine is utilized as the free base or utilized in a salt which has relatively lower solubility. For example, the present application can utilize an insoluble salt such as a fatty acid salt. Representative fatty acid salts include salts of oleic acid or linoleic acid. In preferred embodiments fatty acid salts with between 8 to 20 carbons are used to produce salts with low solubility, such as clonidine palmeate and clonidine stearate. Most preferably, fatty acid salts with between 12 to 18 carbons are used. Other embodiments can utilize a lipid soluble salt of clonidine.

In some embodiments, clonidine can be used with a GABA compound in the drug depot. The GABA compounds used in the treatment methods and in the device include compounds of gamma-aminobutyric acid. Such compounds include gabapentin (2-[1-(aminomethyl)cyclohexyl]acetic acid), pregabalin ((S)-3-(aminomethyl)-5-methylhexanoic acid), vigabatrin (4-aminohex-5-enoic acid), and baclofen (4-amino-3-(4-chlorophenyl)butanoic acid), which are 3'-alkylated GABA compounds. Additional GABA compounds that may be used are described in Satzinger et U.S. Pat. No. 4,024,175; Silverman et al., U.S. Pat. No. 5,563, 175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; WO 02/00209); Silverman et al., PCT Publication No. WO 92/09560; Silverman et al., PCT Publication No, WO 93/23383; Horwell et al., PCT Publication No. WO 97/29101, Horwell et al., PCT Publication No. WO 97/33858; Horwell et al, PCT Publication No. WO 97/33859; Bryans et al., PCT Publication No. WO 98/17627; Guglietta et al., PCT Publication No. WO 99/08671; Bryans et al., PCT Publication No. WO 99/21824; Bryans et al., PCT Publication No. WO 99/31057; WO 98/23383; Bryans et al., J. Med. Chem, 1998, 41, 1838-1.845; Bryans et al., Med. Res. Rev. 1999, 19, 149-177, US Guglietta et al., WO 99/08670; Bryans et al., WO 99/21824; US Bryans et al., UK GB 2 374 595), Belliotti et al., PCT Publication No. WO 99/31074; Bryans et al., PCT Publication No. WO 99/31075; Bryans et al., PCT Publication No. WO 99/61424; Bryans et al., PCT Publication No. WO 00/15611; Bryans, PCT Publication No. WO 00/31020; Bryans et al., PCT Publication No. WO 00/50027; and Bryans et al., PCT Publication No. WO 02/00209). New classes of GABA compounds, which are bicyclic amino acid derivatives, have been recently described by Bryans et al., PCT Publication No. WO 01/28978; Blakemore et al., PCT Pub. No. WO 02/085839; Blakemore et al., U.S. Pat. No. 5,596,900; and Blakemore et al., PCT Pub. No. WO 02/090318. These disclosures are herein incorporated by reference into the present disclosure.

In one embodiment, the GABA compound comprises 1-{[(alpha-isobutanoyloxyethoxy)carbonyl]aminomethyl}-1-cyclohexane acetic acid, baclofen, vigabatrin, gabapentin, pregabalin, gamma-amino-phosphinic acid or 1-{[(alpha-isobutanoyloxyethoxy)carbonyl]aminomethyl}-1-cyclohexane acetic acid, fengabine, GBL (gamma-Butyrolactone), GHB (gamma-Hydroxybutyric acid, 4-hydroxybutanoic acid or sodium oxybate), picamilon and progabide, (s)-(+)-4-amino-3-(2-methylpropyl)-butanoic acid.

In another embodiment, GABA compounds include pharmaceuticals that can increase locally the available amount of endogenous GABA or GABA analogs following their local or systemic administration. These include pharmaceuticals that interfere with GABA or GABA analog reuptake such as tiagabine, stiripentol, deramciclane, hyperforin or a combination thereof. GABA compounds also include pharmaceuticals that interfere with the degradation of GABA or GABA analogs such as phenelzine, gabaculine, valproate, vigabatrin, lemon balm or a combination thereof.

In some embodiments, the GABA compound is released locally from the device at a dose of from about 0.3 mg/day or about 1.8 mg/day or about 3.6 mg/day to about 180 mg/day or about 360 mg/day. In some embodiments, the GABA compound is released from the device at a dose of 0.75 mg to 16 mg per day. In some embodiments, the initial burst or bolus release is about 2 to 20 times higher from 1 hour to about two weeks than the sustained release daily dose released from the device.

In some embodiments, the GABA compound comprises gabapentin, which is released from the device at a dosage of from about 0.3 mg or 1 mg to about 8 mg, 10 mg, 16 mg or 32 mg per day. In some embodiments, the GABA compound comprises pregabalin, which is released from the device at a dosage of from about 0.1 mg or 0.3 mg to about 1 mg, 3 mg, 5 mg or 10 mg per day. In some embodiments, the clonidine can be released from the depot (e.g., fiber, strip, pellet, etc.) at a dose of 0.002 mg to 16 mg per day.

In some embodiments, the ratio of gabapentin to clonidine would be 300:1. For pregabalin, the ratio would be approximately 100:1, in some embodiments, the drug depot releases 300 mg of pregabalin per day.

The GABA compound compliments the anti-inflammatory and analgesic effect of clonidine in the drug depot.

In some embodiments, the drug depot comprises clonidine that is in the drug depot in an amount of from about 0.1% to about 75% by weight.

In some embodiments, the drug depot comprises both a GABA compound and clonidine in a single formulation. In some embodiments, the GABA compound can be in a separate depot (e.g., drug depot) from the clonidine.

In some embodiments, a GABA compound, a steroid, bupivacaine, lidocaine and/or clonidine can be administered in an immediate release or sustained release liquid by injection before, after, or during the administration of the clonidine depot e.g., drug depot).

The clonidine and GABA compound or its pharmaceutically acceptable salt may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the clonidine and/or GABA compound as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogs (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[-4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor (e.g., GDF-5), a LIM mineralization protein, CDMP or progenitor cells or a combination thereof.

Suitable analgesic agents include, but are not limited to, acetaminophen, bupivacaine, lidocaine, opioid analgesics such as buprenorphine, butorphanot, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadoi, codeine, dihydrocodeine, meptazinol, dezocine, eptazocine, flupirtine, amitriptyline, carbamazepine, gabapentin, pregabalin, or a combination thereof.

The therapeutic agent in the drug depot may include, but is not limited to, members of the fibroblast growth factor family, including acidic and basic fibroblast growth factor (FGF-1 and FGF-2) and FGF-4, members of the platelet-derived growth factor (PDGF) including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the drug depot comprises osteogenic proteins. Exemplary osteogenic proteins include, but are not limited to, OP-1, OP-2, OP-3, BMP-2, BMP-3b, BMP-4, BMP-5, BMP-6, BMP-9, BMP-10, BMP-11, BMP-12, BMP-13, BMP-14, BMP-15, GDF-1, GDF-2, GDF-5, GDP-6, GDF-7, GDF-8, GDF-1.0, GDF-11, GDF-12, CDMP-1, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vgl, Ygr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

The clonidine may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot e.g., fiber, strip, pellet, etc.) will be a solid or semi-solid formulation comprised of a biocompatible material that can be biodegradable.

In some embodiments, the implantable medical device comprises a drug depot. In various embodiments, a plurality of drug depots (e.g., pellets) can be administered to a surgical site.

In some embodiments, a plurality of drug depots are provided (e.g., in a kit) and administered to a surgical site and triangulate and/or surround the site to treat post-operative pain. In various embodiments, a plurality of drug depots comprise about 1, 2, 3, 4, 5, 6, 7, 9 or 10 drug depots.

Exemplary excipients, plasticizers, and/or pore forming agents that may be formulated with clonidine in addition to the biodegradable polymer include but are not limited to MgO (e.g., 1 wt. %), MPEG, propylene glycol, mannitol, trehalose, TBO-Ac, Span-65, Span-85, pluronic F127, sorbitol, cyclodextrin, maltodextrin, pluronic F68, CaCl, dextran, dextran sulphate, dextran phosphate, hydroxypropyl-cellulose, ethylcellulose, PEG 1500, PEG 400, PEG3350 or combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

In some embodiments, the drug depot material may have a melting point or glass transition temperature close to or higher than body temperature, but lower than the decomposition or degradation temperature of the therapeutic agent. However, the predetermined erosion of the depot (e.g., drug depot) material can also be used to provide for slow release of the loaded therapeutic agent(s). Non-biodegradable polymers include but are not limited to PVC and polyurethane. In some embodiments, a plasticizer is used to lower glass translation temperature in order to affect stability of the drug depot.

In various embodiments, the drug depot comprises clonidine, bupivacaine or lidocaine and a biodegradable polymer in amorphous, crystalline or semicrystalline form; where the crystalline form may include polymorphs, solvates or hydrates.

In some embodiments, the clonidine can be in powdered form having a particle size predominantly in a range from about 3.5 to about 10 micrometers that can be reconstituted with the polymer for delivery.

In some embodiments, the drug depot has a modulus of elasticity in the range of about $5 \times 10^5$ dyn/cm$^2$. In some embodiments, the drug depot is in the form of a solid. In some embodiments, the drug depot comprises clonidine, bupivacaine or lidocaine.

In some embodiments, the clonidine, bupivacaine, lidocaine, and/or GABA compound is administered in a drug depot that is solid or in semi-solid form. The solid or semi-solid form of the drug depot may have a pre-dosed viscosity in the range of about 1 to about 2000 centipoise (cps), 1 to about 200 cps, or 1 to about 100 cps. After the solid or semi-solid drug depot is administered to the target site, the viscosity of the semi-solid or solid drug depot will increase and the semi-solid will have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the semi-solid or solid drug depot may comprise a polymer having a molecular weight, as shown by the inherent viscosity, from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the drug depot may comprise an 8% loaded 60:40 LCL 5A with a 6.5% content having a 0.4 mm diameter; an 8% loaded 60:40 LCL 5A with a 6.6% content having a 0.8 mm diameter; or a 16% loaded 60:40 LCL 5A with a 13.2% content having a 0.6 mm diameter.

In various embodiments, the depot (e.g., fiber, strip, pellet, etc.) may comprise a bioerodible, a bioabsorbable, and/or a biodegradable biopolymer that may provide immediate release, or sustained release of the clonidine. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), poly(esteramide)s, polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide-caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the drug depot comprises biodegradable polymers comprising wherein the at least one biodegradable polymer comprises one or more of poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

Mannitol, trehalose, dextran, mPEG and/or PEG may be used as a plasticizer for polymer. These plasticizers impart malleability to the resulting formulations. In some embodiments, the polymer and/or plasticizer may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot (e.g., fiber, strip, pellet, etc.). In some embodiments, the range of the coating on the drug depot ranges from about 5 microns to about 250 microns or 5 microns to about 200 microns to delay release from the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caproluctone), poly(D-lactide-co-caprolactone), poly(D,L-lactide), poly(D-lactide), poly(L-lactide), poly(esteramide) or a combination thereof and has an inherent viscosity of 0.2 to about 0.5 dL/gm or 0.6 to about 1.0 dL/gm and a MW of 30,000 to about 125,000 Da.

In some embodiments, the drug depot comprises one or more polymers (e.g., PLA, PLGA, etc.) having a MW of from about 15,000 to about 150,000 Da, from about 25,000 to about 100,000 Da or from about 30,000 to about 50,000 Da.

As persons of ordinary skill in the art are aware, in some embodiments, when implantable depot (e.g., fiber, strip, pellet, etc.) compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot (e.g., fiber, strip, pellet, etc.) composition having a regulated burst index and duration of delivery. For example, a depot (e.g., fiber, strip, pellet, etc.) composition having a polymer with a L/G ratio of 50:50 may have a short duration of delivery ranging from about two days to about one month; a depot (e.g., fiber, strip, pellet, etc.) composition having a polymer with a L/G ratio of 65:35 may have a duration of delivery of about two months; a depot (e.g., fiber, strip, pellet, etc.) composition having a polymer with a L/G ratio of 75:25 or L/CL ratio of 75:25 may have a duration of delivery of about three months to about four months; a depot (e.g., fiber, strip, pellet, etc.) composition having a polymer ratio with a L/G ratio of 85:15 may have a duration of delivery of about five months; a depot (e.g., fiber, strip, pellet, etc.) composition having a polymer with a L/CL ratio of 25:75 or PLA may have a duration of delivery greater than or equal to six months; a depot (e.g., fiber, strip, pellet, etc.) composition having a terpolymer of CL/G/L with G greater than 50% and L greater than 10% may have a duration of delivery of about one month and a depot (e.g., fiber, strip, pellet, etc.) composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot (e.g., fiber, strip, pellet, etc.) compositions having a blend of polymers having different molecular weights, end groups and comonomer ratios can be used to create a depot (e.g., fiber, strip, pellet, etc.) formulation having a lower initial burst and a regulated duration of delivery.

The depot (e.g., fiber, strip, pellet, etc.) may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot (e.g., fiber, strip, pellet, etc.) is to be placed in the spinal area, in various embodiments, the depot (e.g., fiber, strip, pellet, etc.) may comprise sterile preservative free material.

The depot (e.g., fiber) can be different sizes, shapes and configurations. There are several factors that can be taken into consideration in determining the size, shape and configuration of the drug depot. For example, both the size and shape may allow for ease in positioning the drug depot at the target tissue site that is selected as the implantation. In addition, the shape and size of the system should be selected so as to minimize or prevent the drug depot from moving after implantation. In various embodiments, the drug depot can be shaped like a rod or a flat surface such as a film or sheet (e.g., ribbon-like) or the like. Flexibility may be a consideration so as to facilitate placement of the drug depot.

In various embodiments, the drug depot can be different sizes, for example, the drug depot may be a length of from about 0.5 mm to 50 mm and have a diameter of from about 0.01 to about 4 mm. In various embodiments, as the diameter decreases, the surface area that comes in contact with the bodily fluid of the depot (e.g., fiber, strip, pellet, etc.) increases and therefore release of the drug from the depot (e.g., fiber, strip, pellet, etc.) increases. In various embodiments, the drug depot may have a layer thickness of from about 0.005 to 1.0 mm, such as, for example, from 0.05 to 0.75 mm. In various embodiments, the length of the drug depot is determined based on the length needed to treat the target tissue site.

Radiographic markers can be included on the drug depot to permit the user to position the depot (e.g., fiber, strip, pellet, etc.) accurately into the target site of the patient. These radiographic markers will also permit the user to track movement and degradation of the depot (e.g., fiber, strip, pellet, etc.) at the site over time. In this embodiment, the user may accurately position the depot (e.g., fiber, strip, pellet, etc.) in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot (e.g., fiber, strip, pellet, etc.).

In some embodiments, a drug depot is provided that controls delivery of therapeutic agents to local, target tissues and secures itself to a target tissue site. In some embodiments, the drug depot is a flexible, drug loaded pellet or strip or fiber. In some embodiments, the drug depot is flexible, biodegradable that is loaded with the drug and/or drug coated to provide sustained release of a therapeutic to a local tissue site. In some embodiments, drug release is in days to months. In some embodiments, the drug depot comprises polymers, such as, for example, 10:90 poly(D,L-lactide-co-caprolactone), 85:15 poly(D,L-lactide-co-caprolactone), or 60:40 poly(L-lactide-co-caprolactone). Degradation times for the polymers could be weeks to months. In some embodiments, drugs are used such as, for example, an analgesic, anti-inflammatory and/or steroids, which are coated on the drug depot or uniformly distributed throughout the drug depot.

In some embodiments, the drug depot comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the drug depot has a porosity of at least about 30%, at least about 50%, at least about 60%, at least about 70%, at least about 90%. The pore enhances release of the clonidine for treatment of chronic pain.

In some embodiments, the depot may comprise natural and/or synthetic material. For example, the drug depot may comprise poly(alpha-hydroxy acids), poly(lactide-co-glycotide) (PLGA), polylactide polyglycolide (PG), polyethylene glycol (PEG) conjugates of poly(alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin F analogs, such as alpha tocopheryl acetate, d-alpha tocopheryl succinate, polyglycolide (PGA), D-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA/PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA). MMA and N-vinylpyrrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the depot has a thickness of from 0.25 mm to 5 mm, or from about 0.4 mm to about 2 mm, or 0.4 mm to about 1 mm. In some embodiments, the depot has a length of about 1 mm to about 300 mm or about 5 mm to 200 mm or about 5 mm to about 150 mm.

In some embodiments, the diameter of the depot can range from 0.1 mm to 10 mm. In some embodiments, the diameter of the drug depot can range from 0.1 mm to 5 mm, 0.1 mm to 3 mm or 0.1 mm to 1 mm.

In some embodiments, the depot may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more clonidine compounds) may be disposed on or in the depot by hand by soaking, electrospraying, ionization spraying or impregnating, vibratory dispersion (including sonication), nozzle spraying, compressed-air-assisted spraying, brushing and/or pouring.

In some embodiments, the depot may comprise sterile and/or preservative free material. The depot can be implanted by hand or machine in procedures such as for example, laparoscopic, arthroscopic, neuroendoscopic, endoscopic, rectoscopic procedures or the like. In some embodiments, the initial burst surfaces can be disposed on the edges of the depot so that upon contact with the target tissue site, the edges will begin to release the clonidine. In some embodiments, the body of the depot can comprise dense, entangled polymers and have the clonidine to provide slower release of the clonidine.

Alternatively, the clonidine can be disposed homogenously throughout the depot to provide continuous extended release of the clonidine. In some embodiments, the clonidine can be layered in the depot with some portions having different concentrations to provide burst release and then slower release of the clonidine in areas that have dense crosslinked polymers, such as for example, in the core of the drug depot.

The dosage of clonidine released from the depot may be from approximately 0.0005 to approximately 960 µg/day. Additional dosages of clonidine include from approximately 0.0005 to approximately 900 µg/day; approximately 0.0005 to approximately 500 µg/day g/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 mg/day; approximately 0.001 to approximately 60 µg/day; approximately 0.001 to approximately 55 mg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 .mu.g µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In some embodiments, the therapeutically effective dosage amount (e.g., clonidine dose) and the release rate profile are sufficient to reduce inflammation and/or pain for a period of at least 14 days, for example, 14-90 days, 14-30 days, 14-60 days, 21-90 days, 21-180 days; 14-210 days, or 14 days to 6 months or less than 6 months or 1 year or longer.

In some embodiments, the clonidine depot is designed for a bolus dose or burst dose within 1, 2, or 3 days after implantation to provide an immediate release of the clonidine for treatment of pain and/or inflammation.

In some embodiments, the depot has a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ dynes/cm$^2$ to about $5 \times 10^5$ dynes/cm$^2$.

In some embodiments, the semi-solid or solid depot 10 may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g, or about 1.9 to about 2.5 dL/g.

In some embodiments, the drug depot may have a burst release surface that releases about 10%, 15%, 20%, 75%, 10%, 35%, 45%, to about 50% of the clonidine over 24 or 48 hours.

In some embodiments, the depot comprises a polymer having an average molecular weight of the polymer can be from about 1000 to about 10,000,000 or about 1,000 to about 1,000,000 Da; or about 5,000 Da to about 500,000 Da; or about 10,000 Da to about 100,000 Da; or about 20,000 Da to 50,000 Da or about 60,000 Da to about 80,000 Da.

In some embodiments, when the polymer materials have different chemistries (e.g., high MW DLG 5050 and low MW DL), the high MW polymer may degrade faster than the low MW polymer.

In some embodiments, the depot may comprise a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethy methacrylate), polymethyl-methacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, the depot may comprise gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. In some embodiments, the drug depot may comprise polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof.

In various embodiments, rather than directly admixing the therapeutic agent into the depot, microspheres may be dispersed within the depot, the microspheres being loaded with clonidine. In one embodiment, the microspheres provide for a sustained release of the clonidine.

Microspheres, much like a fluid, may disperse relatively quickly, depending upon the surrounding tissue type, and hence disperse the clonidine. In some situations, this may be desirable; in others, it may be more desirable to keep the clonidine tightly constrained to a well-defined target site. The present disclosure also contemplates the use of adherent gel or adhesive to constrain the depot close to the target tissue site. In this embodiment, an adherent gel or adhesive is used to anchor the depot to the target tissue site. The adherent gel or adhesive can, like the depot, also have the therapeutic agent disposed within it. In this way, the depot and the adhesive release the therapeutic agent (e.g., clonidine, statin, etc.) at or near the target tissue site.

Drug Depot Delivery

It will be appreciated by those with skill in the art that the depot (e.g., fiber, pellet, etc.) can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the device is designed to cause minimal physical and psychological trauma to the patient.

In some embodiments, the depot can be sutured to a target tissue site using a suturing needle. The dimensions of the needle, among other things, will depend on the site for implantation. For example, the width of the muscle planes in different surgical procedures can vary from 1-40 cm. Thus, the needle, in various embodiments, can be designed for these specific areas.

Needles may have different shapes such as for example half curved or ski shaped, ¼ circle, ⅜ circle, ½ circle, ⅝ circle, compound curve or the like. The thickness of the needle will also depend on the site of implantation. In various embodiments, the thickness includes, but is not limited to, from about 0.05 to about 1.655. The gauge of the needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot, the cannula or needle includes dose radiographic markers that indicate location at or near the site beneath the skin, so that the user may accurately position the depot (e.g., fiber) at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot may be steritizable. In various embodiments, one or more components of the drug depot are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity, E-beam sterilization may be used, for example, when the drug depot is included in a gel.

Other methods may also be used to sterilize the depot (e.g., fiber) and/or one or more components of the device, including, but not limited to, gas sterilization, such as, for example, with ethylene oxide or steam sterilization.

In various embodiments, a kit is provided that may include additional parts along with the drug depot combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

In various embodiments, a method for delivering a therapeutic agent into a site of a patient is provided, the method comprising inserting a needle at or near a target tissue site and suturing the drug depot at the target site beneath the skin of the patient. In this way unwanted migration of the drug depot away from the target site is reduced or eliminated.

In some embodiments, the drug depot can be delivered to any site beneath the skin, including, but not limited to, at least one muscle, ligament, tendon, cartilage, spinal disc, spinal foraminal space, near the spinal nerve root, connective tissue, fascia, subcutaneous space, or spinal canal.

In some embodiments, it is preferable to co-administer clonidine with an antagonist to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

Another embodiment is directed to a method for treating a mammal suffering from pain, said method comprising administering a therapeutically effective amount of clonidine at a target site beneath the skin. The clonidine (or pharmaceutically acceptable salt) may for example be administered locally to the target tissue site disposed within or on a drug depot.

In some embodiments, the clonidine is encapsulated in a plurality of matrices comprising microparticles, microspheres, microcapsules, and/or microfibers and then put into a drug depot.

In some embodiments there is a method for making an implantable drug depot. The method may comprise combining a biocompatible polymer and a therapeutically effective amount of clonidine or a pharmaceutically acceptable salt thereof and forming the implantable drug depot from the combination.

Method of Making the Depot

In various embodiments, the drug depot comprising the clonidine can be made by combining a biocompatible polymer and a therapeutically effective amount of clonidine or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot (e.g., fiber, pellet, strip, etc.) to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. In dissolved or dispersed form. This results in a polymeric drug depot region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot (e.g., fiber, pellet, strip, etc.) or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, Banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the clonidine containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot (e.g., fiber) is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min.). It is noted that this processing temperature is well below the melting points of clonidine because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot (e.g., fiber, Pellet, strip, etc.) is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric drug depot layers or regions that have permeability to fluids to allow immediate and/or sustained drug release). Multi-region depots (e.g., fibers, pellet, strip, etc.) can also be formed by other processing and shaping techniques such as co-injection or sequential injection molding technology.

In various embodiments, the depot (e.g., fiber, pellet, strip, etc.) that may emerge from the thermoplastic processing (e.g., pellet) is cooled. Examples of cooling processes include air cooling and/or immersion in a cooling bath. In some embodiments, a water bath is used to cool the extruded depot (e.g., fiber, pellet, strip, etc.). However, where a water-soluble therapeutic agent such as clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot (e.g., fiber) surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot (e.g., fiber) to the desired shape. In various embodiments, clonidine is used and mixed or sprayed with the PLGA or PEG550 polymer, and the resulting depot (e.g., fiber) may be formed by extrusion and dried.

In various embodiments, there is a pharmaceutical formulation comprising: clonidine, wherein the clonidine comprises from about 0.1 wt. % to about 40 wt. % of the formulation, and at least one biodegradable polymer. In some embodiments, the clonidine comprises from about 3 wt. % to about 20 wt. %, about 3 wt. % to about 18 wt. %, about 5 wt. % to about 15 wt. %, 0.1 wt % to about 10 wt %, about 0.1 wt % to about 3 wt %, or about 7.5 wt. % to about 12.5 wt. % of the formulation. By way of example, when using a 5%-15% clonidine composition, the mole ratio of clonidine to polymer would be from approximately 16-53 when using an approximately 80 kDalton polymer that has a 267 grams/mole ratio. By way of another example, when using a 5%-15% clonidine base in the composition, the mole ratio of clonidine base to polymer would be from approximately 18-61 with a mole mass of 230 g/triol.

In some embodiments, the clonidine can be in the formulation in an amount of about 1%, 5%, 10%, 15%, 20%, 25%, 30%, 15%, or 40% by weight based on the total weight of the formulation.

In some embodiments, the drug depot comprises at least one biodegradable material in a wt % of about 99.5%, 99%, 98%, 97%, 96%, 95%, 94%, 93%, 92%, 91%, 90% 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot (e.g., fiber) and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly-lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size (e.g., clonidine) is from about 5 to 30 micrometers, or about 2 microns to about 20 microns, or from 30 microns to 100 microns, however, in various embodiments ranges from about it micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers. In some embodiments, at least 80% of the particles have a size from 5 microns to about 100 microns on a volume basis.

In some embodiments, at least 75% of the particles have a size from about 0.5 micrometer to about 100 micrometers. In some embodiments, at least 85% of the particles have a size from about 0.5 micrometers to about 100 micrometers. In some embodiments, at least 95% of the particles have a size from about 0.5 micrometer to about 100 micrometers. In some embodiments, all of the particles have a size from about 0.5 micrometer to about 100 micrometers. In some embodiments, at least 80% of the particles have a size from 2 microns to about 50 microns on a volume basis.

In some embodiments, there is a pharmaceutical formulation comprising: clonidine, wherein the clonidine is in the form of a hydrochloride salt, and comprises from about 0.1 wt. % to about 30 wt. % of the formulation, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 70 wt. % of said formulation.

In some embodiments, the drug depot comprises about 95 wt % poly(D,L-lactide) and 5 wt % clonidine HCl where the polymer has an ester end group and 50,000-70,000 Da MW and an IV 0.45-0.55 dL/g and has a burst release of under 10% of the amount of drug in the depot (e.g., fiber, pellet, strip, etc.) within 24 hours (e.g., 5-10 wt %) or 2-40 mcg in 24 hours. This formulation has 50% of total cumulative dose remaining for at least 60 days. About 80% of the particles in this depot (e.g., fiber) including the clonidine are from about 5 to about 150 microns or 5-100 microns. The depot (e.g., fiber) releases about 0.5 mcg/day up to about 5 mcg/day of clonidine in 24 hours and then continues release for 70 days.

In some embodiments, the drug depot comprises about 92 wt % poly(D,L-lactide) and 8 wt % clonidine HCl where the polymer has an ester end group and the polymer comprises 50,000-70,000 Da MW and an IV of about 0.45-0.55 dL/g and has a burst release of under 10% of the amount of drug in the depot (e.g., fiber) within 24 hours (e.g., 5-10%) or 5-6 mcg in 24 hours and then 1 to 20 mcg/day with a constant release for about 50 days, and then about 0.1 mcg to about 10 mcg/day for 70 days. This formulation has 50% of total cumulative dose remaining for at least 30-42 days and less than 80% cumulative drug release by 70 days. About 80% of the particles in this depot (e.g., fiber) including the clonidine are from about 5 to about 150 microns or 5-100 microns.

In some embodiments, the drug depot comprises about 85 wt % poly(D,L-lactide) and 15 wt % clonidine HCl where the polymer has an ester end group and the polymer comprises 50,000-70,000 Da MW and an IV of about 0.45-0.55 dL/g and has a burst release of under 10% of the amount of drug in the depot (e.g., fiber) within 24 hours (e.g., 5-10%) or 20-150 mcg in 24 hours and then 5 to 80 mcg/day with a constant release for about 30 days, and then about 0.1 mcg to about 5 mcg/day for 70 days. This formulation has about 80% of total cumulative dose released within 35 days and 20% over several months. About 80% of the particles in this depot (e.g., fiber) including the clonidine are from about 5 to about 150 microns or 5-100 microns.

In some embodiments, there is a pharmaceutical formulation comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (e.g., fiber) (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there are methods for treating acute pain. These methods comprise: administering a pharmaceutical composition to an organism, wherein said pharmaceutical composition (e.g., clonidine) comprises from about 0.1 wt. % to about 30 wt. % of the formulation, and at least one biodegradable polymer. In some embodiments, the loading is from about 0.1 wt % to about 10 wt %, about 0.1 wt % to about 3 wt %, 1 wt % to about 25 wt %, or about 5 wt. % to about 10 wt. %. In some embodiments, the loading is from about 10 wt. % to about 70 wt. %.

In some embodiment there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, when the drug depot is in pellet form and comprises 5%, 8% or 15% clonidine HCL to provide pain relief for chronic conditions (e.g., sciatica) for more than 30 days, one drug depot may not be enough. Therefore, in this embodiment, 1, 2, 3, 4, 5, 6, 7, 8, 9 or 10 pellets may be used to provide sufficient pain relief. These 1-10 drug depots/pellets can be triangulated around the pain generator to provide pain relief.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

In some embodiments, clonidine is released at a rate of 2-3 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near a target tissue site, if clonidine is implanted at multiple sites that triangulate the target site then in some embodiments, the total amount of clonidine at each site is a fraction of the total 300-425 micrograms. For example, one may implant a single dose of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

In some embodiments, clonidine is released at a rate of 7-20 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 900-1050 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 900-1050 micrograms. For example, one may implant a single dose of 975 micrograms at one site, or two separate doses of 650 micrograms at two sites, or three separate dose of 325 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

The dosage of clonidine may be from approximately 0.0005 to approximately 960 μg/day. Additional dosages of clonidine include from approximately 0.0005 to approximately 900 μg/day; approximately 0.0005 to approximately 500 μg/day; approximately 0.0005 to approximately 250 μg/day; approximately 0.0005 to approximately 100 μg/day, approximately 0.0005 to approximately 75 μg/day; approximately 0.001 to approximately 70 μg/day; approximately 0.001 to approximately 65 μg/day, approximately 0.001 to approximately 60 μg/day; approximately 0.001 to approximately 55 μg/day; approximately 0.001 to approximately 50 μg/day; approximately 0.001 to approximately 45 μg/day; approximately 0.001 to approximately 40 μg/day; approximately 0.001 to approximately 35 μg/day; approximately 0.0025 to approximately 30 μg/day; approximately 0.0025 to approximately 25 μg/day; approximately 0.0025 to approximately 20 μg/day; approximately 0.0025 to approximately 15 μg/day; approximately 0.0025 to approximately 10 μg/day; approximately 0.0025 to approximately 5 μg/day; and approximately 0.0025 to approximately 2.5 μg/day. In another embodiment, the dosage of clonidine is from approximately 0.005 to approximately 15 μg/day. In another embodiment, the dosage of clonidine is from approximately 0.005 to approximately 10 μg/day. In another embodiment, the dosage of clonidine is from approximately 0.005 to approximately 5 μg/day. In another embodiment, the dosage of clonidine is from approximately 0.005 to 2.5 μg/day. In some embodiments, the amount of clonidine is between 40 and 600 μg/day. In some embodiments, the amount of clonidine is between 200 and 400 μg/day.

In some embodiments, the therapeutically effective dosage amount (e.g., clonidine dose) and the release rate profile are sufficient to reduce inflammation and/or pain for a period of at least one day, for example, 1-90 days, 1-10 days, 1-3 days, 3-7 days, 3-12 days; 3-14 days; 7-10 days, 7-14 days, 7-21 days, 7-30 days, 7-50 days; 7-90 days, 7-140 days, 14-140 days, 3 days to 135 days, 3 days to 180 days, or 3 days to 6 months or 1 year or longer.

In some embodiments the clonidine in the drug depot is designed for a bolus dose or burst dose within 1, 2, or 3 days after implantation to provide an immediate release of the clonidine for treatment of pain and/or inflammation.

In some embodiments, the clonidine drug depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the clonidine depot (e.g., fiber) is administered by placement into an open patient cavity during surgery.

In some embodiments, the drug depot (i) comprises one or more immediate release layer(s) that is capable of releasing about 5% to about 20% of the clonidine or pharmaceutically acceptable salts thereof relative to a total amount of the clonidine or pharmaceutically acceptable salt thereof loaded in the drug depot (e.g., fiber) over a first period of up to 48 hours and (ii) one or more sustain release layer(s) that is capable of releasing about 21% to about 99% of the clonidine or pharmaceutically acceptable salt thereof relative to a total amount of the clonidine or pharmaceutically acceptable salt thereof loaded in the drug depot (e.g., fiber) over a subsequent period of up to 3 days to 90 days, 150 days, 180 days, or 6 months to 1 year.

In some embodiments, there is a drug depot (e.g., fiber) comprising clonidine or clonidine hydrochloride and a polymer, wherein the polymer is one more of various embodiments, the drug depot (e.g., fiber) comprises poly(lactide-co-glycolide) (PLGA), polylactide (PLA), polyglycolide (PGA), D-lactide, L-lactide, D,L-lactide-co-ε-caprolactone, D,L-lactide-co-glycolide-co-ε-caprolactone or a combination thereof.

In some embodiments, the polymer drug depot of the present application enables one to provide efficacy of the active ingredient that is equivalent to subcutaneous injections that deliver more than 2.5 times as much drug.

In some embodiments, the drug depot comprises a polymer having 65 mol. % poly L-lactide and 35 mol. % caprolactone, where the poly(L-lactide-co-caprolactone) has a MW of 30,000 to 40,000 Da and an IV of about 0.5-0.6 dL/g and has a burst release of under 35% of the amount of drug in the depot (e.g., fiber) within 24 hours (e.g., 5-15% within 4 hours). The drug depot comprises clonidine in an amount of 3-8 wt. %. The drug depot releases 400 mcg to about 1000 mcg for 7 days, which is about 40 mcg/day. This drug depot contains 5-10 wt % mannitol as an excipient. The clonidine has a particle size of 25 microns or less and a 90% volume diameter less than 50 microns. The degradation time in the body is not more than 8 months and the drug depot releases all of the clonidine within 2-4 weeks.

In some embodiments, the drug depot comprises a polymer having 10 mol. % poly D-L-lactide and 90 mol. % caprolactone, where the poly(D,L-lactide-co-caprolactone) has a MW of 50,000 to 125,000 Da and an IV of about 0.6 dL/g and has a burst release of under 25% of the amount of drug in the drug depot within 24 hours (e.g., 5-15% within 4 hours). The drug depot comprises clonidine in an amount of 3-10 wt. %. The drug depot releases 400 mcg to about 1000 mcg for 7 days, which is about 40 mcg/day. This drug depot contains from about 1% to about 5% by weight of mannitol or trehalose as a pore forming agent or plasticizer. The clonidine has a particle size of 5 microns or less and a 90% volume diameter less than 20 microns. The degradation time in the body is not more than 12 months and the drug depot (e.g., fiber) releases all of the clonidine within 2-4 weeks. As you drop the drug load the drug released from the depot (e.g., fiber) is faster.

EXAMPLES

The examples below with respect to certain formulations comprising biodegradable polymeric blends of this application show particularly advantageous results.

In this application several polymeric materials having a polydispersity greater than 2 are prepared by mixing polylactide polymers of having different molecular weight distributions and different intrinsic viscosities.

The codes for the polymers are explained as follows. The first number or numbers refer to monomer mole percentage ratio of DL-lactide (e.g., polylactide) to glycolide (e.g., poly-glycolide). The letter code that follows the first number refers to the polymer(s) and is the polymer identifier. The second number, which follows the letter code for the polymer, is the target IV designator and is 10 times the midpoint of a range in dL/g. The meanings of certain IV designators are reflected in Table A.

The inherent viscosity (IV) designations for the polymers are mentioned in Table A below. In some embodiments, the polymers can have the following inherent viscosities.

TABLE A

| IV Target Designator | IV Range dL/g |
| --- | --- |
| 1 | 0.05-0.15 |
| 1.5 | 0.10-0.20 |

TABLE A-continued

| IV Target Designator | IV Range dL/g |
|---|---|
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |
| 10 | 1.0-1.2 |

The final letter within the code of the polymer is the end group designator. For examples "E" refers to an ester end group, while "A" refers to an acid end group.

Biodegradable polymers that are useful in these examples are described below. 100DL 2E is a polymer that has an inherent viscosity of 0.15-0.25 dL/g and a molecular weight of about 7 kDa. It contains 100% poly(D,L-lactide) that has ester end groups and is available from Evonik Industries, Birmingham, Ala., under the trademark RESOMER®. 100DL 4.5A is polymer that has an inherent viscosity of 0.40-0.50 dL/g and a molecular weight of about 50 kDa. It contains 100% poly(D,L-lactide) that has carboxylic acid end groups and is available from Evonik industries, Birmingham, Ala., under the trademark RESOMER®. 100DL 4.5E is polymer that has an inherent viscosity of 0.40-0.50 dL/g and a molecular weight of about 50 kDa. It contains 100% poly(D,L-lactide) that has ester end groups and is available from Evonik industries, Birmingham. Ala., under the trademark RESOMER®. 100DL 7E is polymer that has an inherent viscosity of 0.60-0.80 dL/g and has a molecular weight from about 80 kDa to about 90 kDa. It contains 100% poly(D,L-lactide) that has ester end groups and is available from Evonik Industries, Birmingham, Ala., under the trademark RESOMER®.

Example 1

In this example, upon mixing 10% by wt. 100DL 2E with 20% by wt. 100DL 4.5A, 50% by wt. 100DL 4.5E and 20% by wt. 100DL WE a polymer blend would be obtained having a polydispersity greater than 2 that results in a polymer degradation time of less than 6 months.

Example 2

This example illustrates another polymer blend which can be obtained by mixing 5% by wt. 100DL 2E with 25% by wt. 100DL 4.5A, 50% by wt. 100DL 4.5E and 20% by wt. 100DL 7E a polymer blend obtains having a polydispersity greater than 2 that will result in a polymer degradation time of less than 6 months.

Example 3

This example illustrates another polymer blend which can be obtained by mixing 5% by wt. 100DL 2E with 25% by wt. 100DL 4.5A, 55% by wt. 100DL 4.5E and 25% by wt. 100DL 7E a polymer blend obtains having a polydispersity greater than 2 that will result in a polymer degradation time of less than 6 months.

Example 4

This example describes another polymer blend which can be obtained by mixing 10% by wt. 100DL 2E with 20% by wt. 100DL 4.5A, 55% by wt. 100DL 4.5E and 15% by wt. 100DL 7E a polymer blend obtains having a polydispersity greater than 2 that will result in a polymer degradation time of less than 6 months.

Example 5

This example describes yet another polymer blend which can be obtained by mixing 10% by wt. 100DL 2E with 15% by wt. 100DL 4.5A, 50% by wt. 100DL 4.5E and 25% by wt. 100DL 7E a polymer blend obtains having a polydispersity greater than 2 that results in a polymer degradation time of less than 6 months.

Example 6

In this example, another polymer blend can be obtained by mixing 10% by wt. 100DL 2E with 20% by wt. 100DL 4.5A, 55% by wt. 100DL 4.5E and 15% by wt. 100DL 7E a polymer blend obtains having a polydispersity greater than 2 that results in a polymer degradation time of less than 6 months.

Having now generally described the invention, the same may be more readily understood through the following reference to the following examples, which are provided by way of illustration and are not intended to limit the present invention unless specified.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A polymeric material comprising a plurality of biodegradable polymers having a polydispersity or molecular weight distribution from about 1.5 to about 2.5, wherein the plurality of biodegradable polymers comprises a first polymer in an amount from about 5% to about 15%, a second polymer in an amount from about 15% to about 25%, a third polymer in an amount from about 45% to about 55%, and a fourth polymer in an amount from about 15% to about 25% by weight, and the first polymer comprises 100% poly(D,L-lactide) having ester end groups, the second polymer comprises 100% poly(D,L-lactide) having carboxylic acid end groups, the third polymer comprises 100% poly(D,L-lactide) having ester groups and the fourth polymer comprises 100% poly(D,L-lactide having ester groups.

2. A polymeric material of claim 1, wherein the plurality of biodegradable polymers have a polydispersity ($M_w/M_n$) of greater than 2.

3. A polymeric material of claim 1, wherein the plurality of biodegradable polymers have a weight-average molecular weight from about 50 kDA to about 70 kDa.

4. A polymeric material of claim 1, wherein the first polymer has an inherent viscosity from about from about 0.15 to about 0.25 dL/g, the second polymer has an inherent viscosity from about 0.40 to about 0.50 dL/g, the third polymer has an inherent viscosity from about 0.40 to about 0.45 dL/g and the fourth polymer has an inherent viscosity from about 0.60 to about 0.80dL/g.

5. A medical device comprising a plurality of biodegradable polymers having a polydispersity or molecular weight distribution from about 1.5 to about 2.5, wherein the plurality of biodegradable polymers comprises a first polymer in an amount from about 5% to about 15%, a second polymer in an amount from about 15% to about 25%, a third polymer in an amount from about 45% to about 55%, and a fourth polymer in an amount from about 15% to about 25% by weight, and the first polymer comprises 100% poly(D,L-lactide) having ester end groups, the second polymer comprises 100% poly(D,L-lactide) having carboxylic acid end groups, the third polymer comprises 100% poly(D,L-lactide) having ester groups and the fourth polymer comprises 100% poly(D,L-lactide having ester groups.

6. A medical device according to claim 5, wherein the biodegradable polymers have a polydispersity or molecular weight of 1.8, 1.9, 2.0, 2.1, 2.2, 2.4 or 2.5.

7. A medical device of claim 5, wherein the medical device further comprises an active pharmaceutical ingredient.

8. A medical device of claim 7, wherein the active pharmaceutical ingredient is present in an amount from about 0.1% to about 20% by weight of the medical device.

9. A medical device of claim 8, wherein the active pharmaceutical ingredient is clonidine in the form of clonidine hydrochloride or a mixture of clonidine base and a hydrochloride salt.

10. A medical device of claim 5, wherein the medical device is an implantable depot.

11. A method of making a polymeric material, the method comprising mixing a plurality of biodegradable polymers together to form a polymeric mixture, wherein the polymeric mixture has a polydispersity from about 1.5 to about 2.5, and the plurality of biodegradable polymers comprises a first polymer in an amount from about 5% to about 15%, a second polymer in an amount from about 15% to about 25%, a third polymer in an amount from about 45% to about 55%, and a fourth polymer in an amount from about 15% to about 25% by weight, and the first polymer comprises 100% poly(D,L-lactide) having ester end groups, the second polymer comprises 100% poly(D,L-lactide) having carboxylic acid end groups, the third polymer comprises 100% poly(D,L-lactide) having ester groups and the fourth polymer comprises 100% poly(D,L-lactide having ester groups.

12. A method of claim 11, further comprising adding a solvent to the polymeric mixture to form (i) a polymeric mixture solvent blend; or (ii) a polymeric mixture in solution.

13. A method of claim 12 further comprising adding an anti-solvent to the polymeric mixture in solution to separate a mixture of biodegradable polymers having polydispersity from about 1.5 to about 2.5.

14. A method of claim 12, wherein the solvent comprises n-hexane, cyclohexane, heptanes, methylene chloride, ethyl acetate, acetone or combinations thereof.

15. A method of claim 13, wherein the anti-solvent comprises water, ethanol, methanol, supercritical carbon dioxide, supercritical nitrogen, supercritical water or mixtures thereof.

16. A method of claim 11, wherein the plurality of biodegradable polymers comprises a first polymer in an amount of about 10%, a second polymer in an amount of about 20%, a third polymer in an amount of about 50% and a fourth polymer of about 20% by weight.

17. A method for treating acute pain in an organism to reduce, prevent or treat pain, the method comprising implanting a depot comprising a plurality of biodegradable polymers, the polymers having a polydispersity or molecular weight distribution from about 1.5 to about 2.5, wherein the plurality of biodegradable polymers comprises a first polymer in an amount from about 5% to about 15%, a second polymer in an amount from about 15% to about 25%, a third polymer in an amount from about 45% to about 55%, and a fourth polymer in an amount from about 15% to about 25% by weight, and the first polymer comprises 100% poly(D,L-lactide) having ester end groups, the second polymer comprises 100% poly(D,L-lactide) having carboxylic acid end groups, the third polymer comprises 100% poly(D,L-lactide) having ester groups and the fourth polymer comprises 100% poly(D,L-lactide having ester groups.

* * * * *